United States Patent [19]

Grawert et al.

[11] 4,237,291

[45] Dec. 2, 1980

[54] PROCESS FOR THE ISOLATION OF ERGOT ALKALOIDS FROM CULTURE SUSPENSIONS

[75] Inventors: Werner Grawert; Ludwig Schiedt, both of Radebeul; Brigitte Neumann, Dresden; Karlheinz Heidenbluth, Radebeul; Christoph Dauth, Radebeul; Rudolf Schirutschke, Radebeul; Monika Müller, Radebeul, all of German Democratic Rep.

[73] Assignee: VEB Arzneimittelwerk Dresden, Radebeul, German Democratic Rep.

[21] Appl. No.: 971,219

[22] Filed: Dec. 20, 1978

[30] Foreign Application Priority Data

Dec. 20, 1977 [DD] German Democratic Rep. ... 202798

[51] Int. Cl.$^3$ .............................................. C07D 519/02
[52] U.S. Cl. .................................... 544/346; 544/361; 424/123; 546/67; 546/68; 546/69
[58] Field of Search .................................... 546/67–69; 544/346, 361; 424/123

[56] References Cited

U.S. PATENT DOCUMENTS

| 2,809,920 | 10/1957 | Stoll et al. | 544/346 |
| 2,835,675 | 5/1958 | Abe et al. | 544/346 |

Primary Examiner—Mary C. Lee
Attorney, Agent, or Firm—Michael J. Striker

[57] ABSTRACT

A process for isolating ergot alkaloids from culture suspensions, in which after mechanical filtration, the residue is dried in a fluidized drying bed and the alkaloids are extracted with an aprotic organic solvent, reextracted with a weakly acidic aqueous solution which is subsequently made basic, and finally extracted with a water-immiscible organic solvent, from which the alkaloids are isolated in a conventional manner. In certain instances, the culture suspension is stirred with an adsorbent clay to entrain the water-soluble alkaloids.

10 Claims, No Drawings

PROCESS FOR THE ISOLATION OF ERGOT ALKALOIDS FROM CULTURE SUSPENSIONS

BACKGROUND OF THE INVENTION

It is characteristic of saprophytic ergot cultures, that the water soluble alkaloids produced, such as ergometrins, clavine, and some peptide alkaloids, are more or less singularly diffused in the cell mass and liquid components. The prior art has dealt with this fact by utilizing different preparative methods for the isolation of the alkaloids from both or either of the components, after separating the cell mass from the culture filtrate (HU-PS No. 150,632; HU-PS No. 161,654; as well as HU-PS No. 150,631; DL-PS No. 41,967; OE-PS No. 250,770).

These methods take into account the special solubility characteristics of the desired alkaloids. Thus, in the Hungarian Application No. R I-440, the addition of in some instances considerable quantities of salts is used to isolate the water-soluble ergometrin. The process described in HU-PS No. 142,407, an adsorption on bentonite with a subsequent extraction of the adsorbate with aqueous alcohol, proved to be undesirable on account of substantial losses through isomerization (in this context, see also HU-PS No. 142,406).

It was therefore not considered worth investigating the development of an entrainment process for isolating the alkaloids from the culture suspension; a direct extraction from the suspension was one of the alternatives investigated, in DDR Pat. No. 12d/165,516. The development of emulsions and a tendency for the alkaloids to isomerize in dependence on the timing of the isolation procedure, however, diminished the practical value of this process.

DESCRIPTION OF THE INVENTION

An object of this invention is the development of an economical procedure for the isolation of all types of ergot alkaloids in saprophytic cultures which overcome the disadvantages of the prior art processes. This is achieved through the employment of the entrainment principle.

It has been found surprisingly, that adsorbent clays such as bentonite, nontronite, bleaching earth, and fuller's earth have an unusually high adsorption capacity at the natural pH value of the culture suspension not only for the ergometrin, but for all the investigated ergot alkaloids of the most diverse structures.

It has further been discovered that the mycella-adsorbent mixture can be separated from the liquid component in a relatively facile manner through filtration or other physical separation means.

A still further surprising discovery was that after physical separation, the mycella-adsorbent mixture containing the alkaloids can be subjected to fluidized bed drying according to the known physical parameters at the normally unfavorably high temperature for the alkaloids of 80°–90° C. without isomerization or decomposition of the compounds. After a washing with a weak aqueous alkaline solution, the alkaloids can then be extracted easily and virtually completely from the dry mycella-adsorbent mixture with an organic aprotic solvent.

In further investigations it was determined that this drying process was also applicable to those cultures in which the alkaloids are contained in the cell mass; thus, the addition of the adsorbent in these systems was not necessary. In this case, after mechanical separation and drying in the fluidized bed, dry mycella containing the alkaloid are obtained, the further work-up of which is not dependent upon the time of the termination of the drying process, unlike in the prior art.

This inventive process can be used to isolate a whole spectrum of ergot alkaloids, such as ergocryptine, ergotamine, ergocristine, ergocornine, ergometrine, lysergic acid, agroclavine, ergosine and others. This is achieved through the addition of 4–5% by weight, based on the water soluble recovered material, of an adsorbent clay and stirring for about 30 minutes. After mechanical separation of the solid material, for example through filtration, the wet mycella-adsorbent mixture is placed in a fluidized drying bed at 80°–90° C. for about 20 to 40 minutes until an exhaust temperature of between 50° and 70° C. and a residual moisture content of no more than about 15% is achieved. The mycella-adsorbent mixture is then mixed with an aqueous, weakly alkaline solution, for example, 15% ammonia water, and then extracted with an aprotic organic solvent, for example, a lower carboxylic acid ester, acetone or a halogenated hydrocarbon. This extract is then further treated by liquid-liquid extraction with an aqueous acidic phase in a ratio of 2:1 to 1:1 by volume, in order to eliminate the non-basic residue. The aqueous solution containing the total alkaloid content is then made basic to a pH in the range of 8 to 9.5 and the alkaloids are extracted with an organic solvent not miscible with water, preferably ethyl acetate, in a ratio of 1:1 to 3:1 by volume.

The further treatment of the extract follows the known procedure with recognition of the chemical and physical properties of the alkaloids.

Bentonite is a montmorillonite-containing clay, named after its source, Fort Benton, Mont. It is among the group of clays commonly referred to as bleaching earths which require activation by an acidic treatment process. Fuller's earth, another montmorillonite-containing clay, is not treated by any activation process before use; hence its description as a "raw bleaching earth". These and other adsorbent clays may be employed in the inventive process.

The novel features which are considered as characteristic for the invention are set forth in particular in the appended claims. The invention itself, however, will be best understood from the following description of preferred embodiments:

EXAMPLE 1

200 l Of culture suspension of Claviceps purpurea (Fr.), Tul. IMET PA 130 (obtained from the Jena Central Institute for Microbiology and Experimental Therapy, GDR) is stirred for 30 minutes with 8 kg bentonite. It is then filtered through a 10 mm layer of calcium sulfate dihydrate over a rotary vacuum cell filter; the practically alkaloid-free filtrate is discarded. The recovered mycella-bentonite mixture is dried in a fluidized bed at an influx temperature of 90° C. until an exhaust temperature of 60° C. is achieved. This takes approximately 30 minutes. There is recovered 20–24 kg of mycella-bentonite mixture with a residual moisture content of from 3–5%; this mixture contains 95–100% of the ergotoxin and 92–96% of the ergometrin contained in the culture suspension.

EXAMPLE 2

100 l Of the culture suspension of Example 1 is stirred for 1 hour with 5 kg of bleaching earth, filtered, and the mycella-adsorbate mixture is dried in the fluidized bed at 80°–90° C. for about 15 minutes until an exhaust temperature of 50° C. is reached. There is recovered 12 kg of the dried mycella-adsorbent mixture with a residual moisture content of 10–12% and an alkaloid content of 92–100% based on the culture suspension.

EXAMPLE 3

10 kg Of the dry mycella-adsorbent mixture of either Example 1 or 2 is stirred with 1.5 l of 1:2 diluted ammonia. After about 5–10 minutes it is mixed in an Ultra-Turrax for at least 15 minutes with 40 l ethyl acetate in two portions. The total extract is sent through a separator, such as Model SA 7-01-076 of the German firm Westfalia in Oelde, FRG, with 20 l of 3% aqueous phosphoric acid. The heavy phase is mixed with 8 l of ethyl acetate, and stirred for 10 minutes with additions of concentrated ammonia to a pH of 8.5–9.0. After separation of the phases the extraction is repeated twice with 6–8 l of ethyl acetate. The total extract is concentrated on a rotary evaporator or similar condensing device to 0.3–0.6 l. The concentrate is mixed with a double volume of chloroform adduct. After chromatographic purification the ergotoxin is recovered from the filtrate as the benzolor toluol-adduct, by column or batch adsorption. Both adducts are thin-layer chromatographically pure and have an alkaloid content of 96 to 103% calculated as the bimaleinate. The yield is 58.6 g ergotoxin-toluol adduct, 72% calculated from the culture suspension and 40.5 g ergometrin-chloroform adduct, 82% from the suspension.

EXAMPLE 4

60 kg Of the dry mycella-adsorbent mixture of Example 1 or 2 is mixed with 7.5 l of 1:1 diluted ammonia, extracted in a mechanical extractor with 150 l chloroform or methylene chloride over 45 minutes, filtered under pressure and the process repeated with the same volume of solvent for 30 minutes. The total extract is added to an equal volume of 5% aqueous acetic acid and processed in a separator, the aqueous phase constantly adjusted to pH 9; the process is repeated a second time with the same solvent or with ethylene acetate at a double volume. After evaporation and isolation of the ergometrin and ergotoxin, the adducts and yields of Example 3 are obtained.

EXAMPLE 5

30 l Culture solution of Claviceps purpurea IMET PA 134 at its natural pH value (5–6) is stirred for 30 minutes with 1.2 kg bentonite. It is then filtered through a layer of calcium sulfate dihydrate and the filtrate discarded. Drying of the mycella-adsorbent mixture according to Example 1 yields 2.8 kg of the dry mixture, which contains practically all of the alkaloid content of the culture suspension (ergosine, ergosinine, traces of chanoclavine). Rotary extraction of the alkaloids with a 10 to 12 fold volume of ethyl acetate yields up to 90% of the alkaloid content of the dry mycella-bentonite mixture.

EXAMPLE 6

20 l Culture suspension of Example 5 is filtered without addition of adsorbent over 20 mm of calcium sulfate dihydrate; the filtrate, which contains traces of ergosine and a portion of the other alkaloids is discarded. The isolated mycellas are immediately dried in the fluidized drying bed at 90° C. for about 40 minutes until the exhaust temperature reaches 60° C. 0.8–1.0 kg of the dry mycellas containing 96–100% of the ergosine of the culture suspension as well as traces of the other alkaloids. The dry mycellas are stirred with 150 ml 10% ammonia and extracted with 8 l chloroform in two portions. After extraction into an aqueous acidic phase, re-extraction and evaporation, the acetic acid salt precipitates.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process for isolating ergot alkaloids from a raw culture suspension, comprising stirring said suspension with an absorbent clay selected from the group consisting of fuller's earth, bentonite and a bleaching earth; mechanically filtering said suspension, thereby isolating a filtration residue including said absorbent clay; drying said residue in a fluidized drying bed at a temperature of about 80°–90° C. for about 20 to 40 minutes until an exhaust temperature of about 50°–70° C. is achieved; treating the dried residue by extraction with an aprotic organic solvent; extracting from said aprotic organic solvent basic compounds with a weakly acidic aqueous solution; treating said weakly acidic aqueous solution with base to form a basic solution; treating said basic solution by extraction with an organic solvent which is immiscible in water; and isolating said ergot alkaloids from said water-immiscible organic solvent.

2. A process for isolating ergot alkaloids from a raw culture suspension, in which said alkaloids are contained predominantly within culture cell mass, comprising mechanically filtering said suspension, thereby isolating a filtration residue; drying said residue in a fluidized drying bed at a temperature of about 80°–90° C. for about 20 to 40 minutes until an exhaust temperature of about 50°–70° C. is achieved; treating the dried residue by extraction with an aprotic organic solvent; extracting from said aprotic solvent basic compounds with a weakly acidic aqueous solution; treating said weakly acidic aqueous solution with base to form a basic solution; treating said basic solution by extraction with an organic solvent which is immiscible in water; and isolating said ergot akkaloids from said water-immiscible solvent.

3. A process as defined in claim 1, wherein said stirring is effected for about 30 minutes.

4. A process as defined in claim 1, wherein said adsorbent clay comprises about 4–5% by weight.

5. A process as defined in claim 1, wherein said filtration residue is dried until a residual moisture content of less than about 15% is achieved.

6. A process as defined in claim 1, wherein said aprotic organic solvent is a low molecular weight carboxylic acid ester, preferably ethyl acetate, acetone or a halogenated hydrocarbon.

7. A process as defined in claim 1, further comprising treating said dried residue with an approximately 10–20% by weight aqueous alkaline solution, preferably ammonia, before extraction with said aprotic organic solvent.

8. A process as defined in claim 1, wherein said weakly acidic aqueous solution is an approximately 3–5% solution of phosphoric or acetic acid, used in a volume of about 2:1 to 1:1 relative to said aprotic organic solvent.

9. A process as defined in claim 1, wherein said weakly acidic aqueous solution is treated to achieve a pH of between about 8.0–9.5.

10. A process as defined in claim 1, wherein said water-immiscible organic solvent is a low molecular weight carboxylic acid ester, preferably ethyl acetate or a halogenated hydrocarbon, preferably chloroform or methylene chloride, used in a volume of 3:1 to 1:1 relative to said basic solution.

* * * * *